United States Patent [19]

Orth et al.

[11] Patent Number: 5,316,729
[45] Date of Patent: May 31, 1994

[54] ERYTHROCYTE SEDIMENTATION RATE MEASURING APPARATUS

[76] Inventors: Helmut Orth, Ludwigsburger Str. 78, D-W7120 Bietigheim-Bissingen; Joachim Horrer, Stöcklestr. 13, D-W7400 Tubingen, Fed. Rep. of Germany; Dietmar Holst, Schurwaldstr. 4, D-W7327 Adelberg, all of Fed. Rep. of Germany

[21] Appl. No.: 982,313

[22] Filed: Nov. 27, 1992

[51] Int. Cl.$^5$ .............................................. G01N 33/00
[52] U.S. Cl. .................... 422/73; 422/82.05; 436/70; 73/864.01; 73/61.63; 73/61.65; 73/61.66; 73/61.69
[58] Field of Search ............. 422/73, 82.05, 101; 73/864.01, 61.63, 61.65, 61.66, 61.69; 436/70

[56] References Cited

U.S. PATENT DOCUMENTS

| | | | |
|---|---|---|---|
| 3,754,866 | 8/1973 | Ritchie et al. | 422/73 |
| 4,684,265 | 3/1987 | Sarsedt | 73/61.4 |
| 4,701,305 | 10/1987 | Hattori et al. | 422/73 |
| 4,720,787 | 1/1988 | Lipscomb | 364/413.07 |
| 4,822,568 | 4/1989 | Tomita | 422/73 |
| 4,848,900 | 7/1989 | Kuo et al. | 356/39 |
| 4,876,069 | 10/1989 | Jochimsen | 422/73 |
| 4,964,728 | 10/1990 | Kloth et al. | 422/73 |
| 5,003,488 | 3/1991 | Hardy | 364/509 |

FOREIGN PATENT DOCUMENTS

| | | |
|---|---|---|
| 2353272 | 5/1975 | Fed. Rep. of Germany . |
| 2442877 | 3/1976 | Fed. Rep. of Germany . |
| 2706871 | 8/1977 | Fed. Rep. of Germany . |
| 2631291 | 1/1978 | Fed. Rep. of Germany . |
| 2757039 | 6/1979 | Fed. Rep. of Germany . |
| 3520962 | 12/1985 | Fed. Rep. of Germany . |
| 3609552 | 8/1987 | Fed. Rep. of Germany . |
| 3640164 | 6/1988 | Fed. Rep. of Germany . |

Primary Examiner—James C. Housel
Assistant Examiner—N. Bhat
Attorney, Agent, or Firm—Fred Philpitt

[57] ABSTRACT

An apparatus for measuring the erythrocyte sedimentation rate comprising a measuring head having at least light barrier, which can be moved along a test cell containing a blood sample. The output signals of light detectors (52, 54, 60) of the light barriers are fed to an evaluating processor (74), which continuously compares the profiles of the optical density obtained at different measuring times with various reference curves having a known final value of the position of the interphase between the serum and the blood cake.

8 Claims, 4 Drawing Sheets

ERYTHROCYTE SEDIMENTATION RATE MEASURING APPARATUS

The invention relates to an erythrocyte sedimentation rate measuring apparatus.

Such a measuring apparatus has been disclosed in DE-A1-36 40 164. Due to the optoelectronic determination of the sedimentation rate more precise values are obtained than in previous apparatus, wherein the position of the interphase defined between the serum and the sedimented blood corpuscles was visually measured using a scale. More particularly, DE-A1-36 40 164 discloses a measuring apparatus, wherein the test cells containing the blood can be inserted into a measuring head and removed from such measuring head without the danger of damaging this head.

DE-A1-36 40 164 discloses no details as to evaluation of the signals output from the measuring head of this known measuring apparatus.

The sedimentation process of the erythrocytes in the test cell takes a very long time. The object of the present invention is to improve a measuring apparatus so rapid reliable information on the presumable final value of the position of the interphase defined between the serum and the blood cake is obtained.

In the measuring apparatus in accordance with the present invention the dynamics of the sedimentation process are used for extrapolating the final value of the position of the interphase between the serum and the blood cake, which is achieved by continuously fitting the already measured portion of the sedimentation curve to at least one reference curve, for which the final value of the position of the interface is known.

The continuous detailed evaluation of the sedimentation process in addition furnishes supplemental information, which has been neglected in the previous coarse evaluating methods. Thus particularly the very first part of the sedimentation process, wherein no distinct interphase between the serum and the blood cake has formed yet, is a finger print of the blood sample to be examined. Particularly in this first portion of the sedimentation curve there are not only quantitative but also qualitative differences, which show up in the exact evaluation of the sedimentation process.

A measuring apparatus in accordance with one embodiment will provide valuable supplemental information on the physical condition of the patient via the type of that reference curve which best fits the momentarily measured sedimentation process. In addition, the use of qualitatively different reference curves warrants more reliable extrapolation of the final value of the position of the interphase.

In a measuring apparatus in accordance with one embodiment the additional information is reduced to a few data of interest to a doctor, who is not familiar with the details of the sedimentation process.

As has been pointed out above, the profile of the optical density of the blood sample measured along the vertical extension of the test cell contains valuable supplemental information going beyond the information deductible from the mere position of the interphase. The optical density undergoes considerable changes during the sedimentation process. In accordance with another embodiment a measuring apparatus can equally well evaluate in quantitative manner changes in the optical density in the region of small, intermediate and large optical density, since in these regions the output of a respective light barrier is used, the light of which is absorbed strongly, in an average way or weekly, only.

A measuring apparatus in accordance with another embodiment allows for a simple comparison of the measured density profile with typical density profile reference curves, which is of importance in view of obtaining additional information as well as in view of reliable extrapolation of the final value of the position of the phase interphase, since for this extrapolation not only the final value "position of the interphase" is used but the entire density profile.

In a measuring apparatus in accordance with another embodiment contributions of portions of the blood column neighboring the wall of the test cell, which are affected by perturbing effects like adhesion, are automatically discarded, since the test cell also acts as a cylinder lens, by which rays passing through the marginal portions of the test cell are so strongly deflected, that they will not any longer reach the light detector of the light barrier arrangement, which is of small dimension.

In a measuring apparatus in accordance with another embodiment the relative movement effected between the measuring head and the test cell for determining the sedimentation rate is also used for reading out a bar code attached to the respective test cell and identifying the respective patient. Thus the measuring apparatus automatically recognizes a newly inserted test cell without requiring input of data by the operating person and will start the measuring program for this test cell. Furthermore wrong correspondences between blood samples and patients are eliminated this way.

The just mentioned way of avoiding mixing up of blood samples also allows to further improve the measuring apparatus in accordance with another embodiment such that it is formed with a plurality of recesses each adapted to receive a test cell and to intermittently move them to an operating position, wherein they are aligned with the path of the measuring head. To this end a turn table or an endless conveyor may be provided, which will index the test cell receptacles.

A preferred embodiment of the invention will now be explained in more detail referring to the drawings. Therein:

BRIEF DESCRIPTION OF THE DRAWINGS

In FIG. 1 a base structure of an erythrocyte sedimentation rate measuring apparatus is generally shown at 10. A vertical shaft 12 is journalled in the base structure 10, the lower end of which is driven by an electromotor 16 via a worm gear drive 14. The lower end of the shaft 12 is connected to a turn table 18, being formed with eight recesses 20 arranged under equal angular distance. Each recess 20 is adapted to receive the lower end of a slim cylindrical test cell 22, which will receive a blood sample, respectively. The upper ends of the test cells 22 are positioned by slotted resilient fixing arms 24 connected to a support disc 26, which is secured to the upper end of shaft 12.

Figure 1:
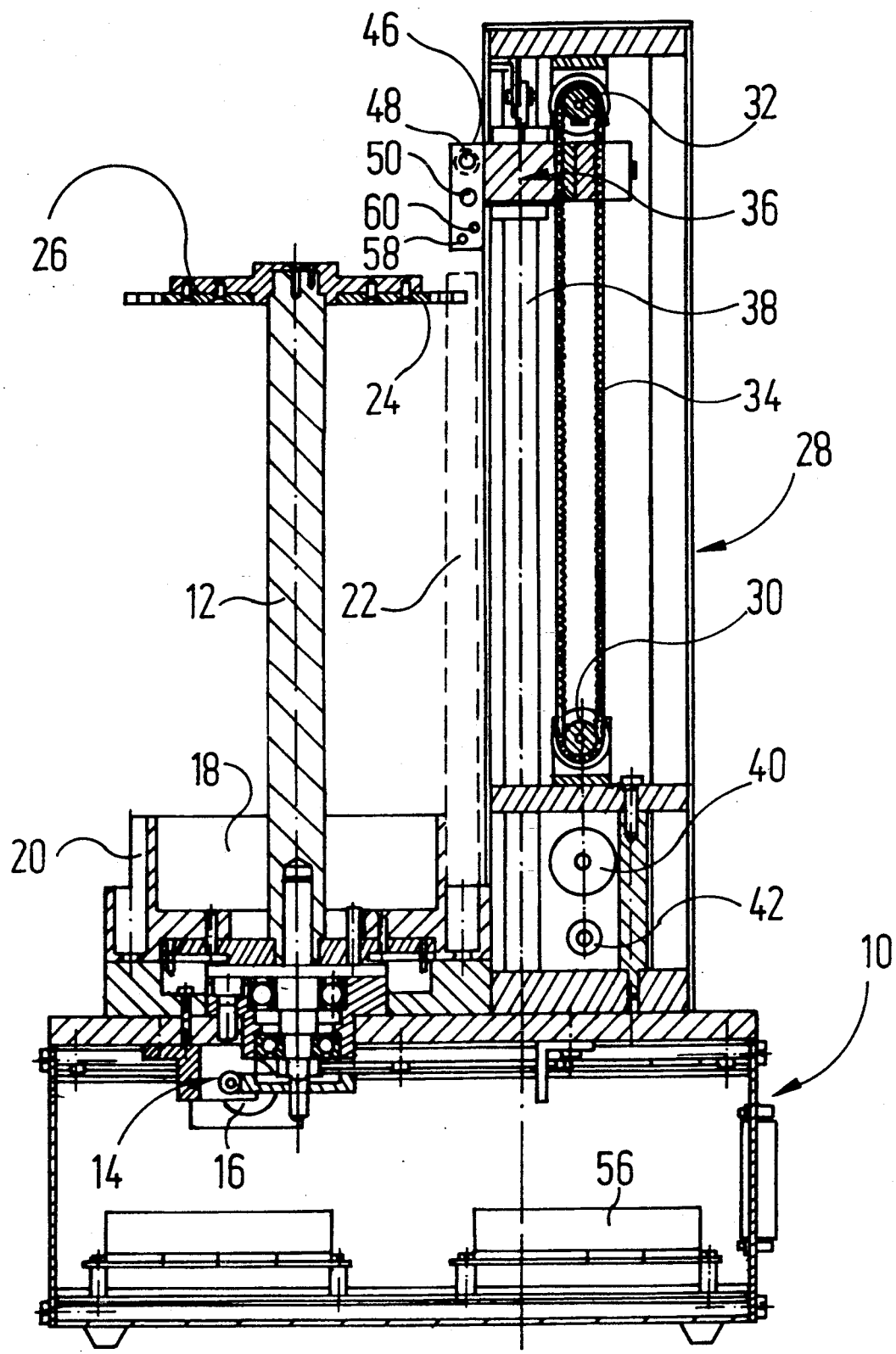
FIG. 1: is a vertical longitudinal section through an apparatus for measuring the erythrocyte sedimentation rate, the section being taken along line I—I of FIG. 2.
Figure 2:
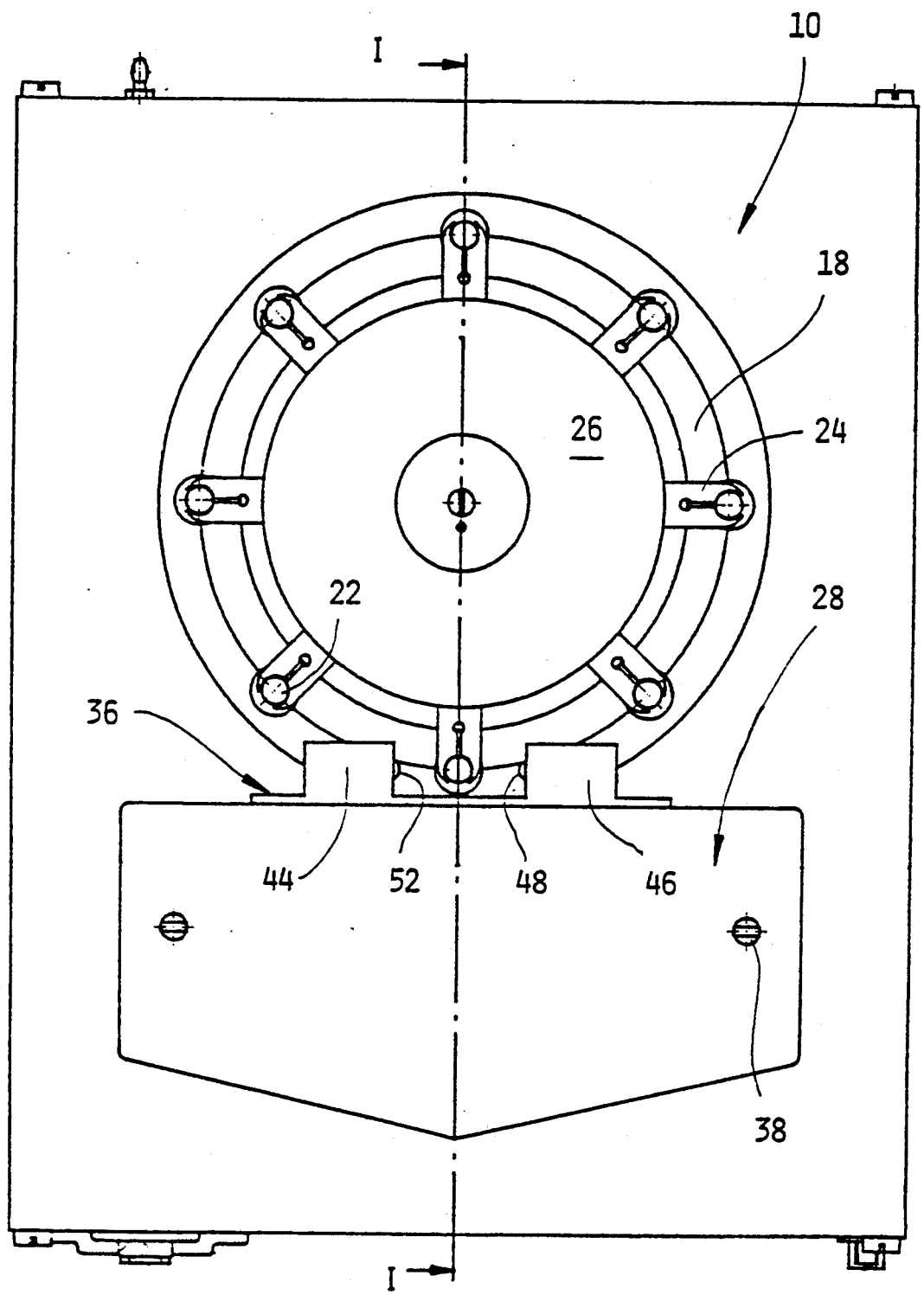
FIG. 2: is a top view of the measuring apparatus shown in FIG. 1.

In a measuring housing generally shown at 28, a lower deflection pulley 30 as well as an upper deflection pulley 32 are journalled, a tooth belt 34 running over these pulleys. The run of the tooth belt 34 being the left hand run of FIG. 1 is fixedly ted to measuring head 36 running on two lateral guide bars 38. The lower deflection pulley 30 is driven by an electric motor 40, the shaft of which is also connected to an incremental rotary position sensor 42 (e.g. disk formed with a plurality of slots or the like).

The measuring head 36 is formed with two legs 44, 46 being symmetric with respect to the median plane thereof which are movable along a test cell standing in front of the measuring head housing 28 on either side thereof. In the upper end position of the measuring head 36, which is shown in FIG. 1, the support disc 26 and the upper ends of the test cells can be freely moved on a path extending below the measuring head 36.

The leg 46 of the measuring head 36 carries a light emitting diode (LED) 48 providing red light as well as a LED 50 being arranged therebelow and emitting green light. Opposing these light sources the leg 44 carries a phototransistor 52 and a phototransistor 54 (shown only in FIG. 3). These two pairs of elements formed by a LED and a photo transistor, respectively, each form a light barrier, the LED 48 and the LED 50 being energized from a supply unit 56 arranged in the base structure 10 by alternating current of predetermined frequency.

A further LED 58 is arranged in the leg 46 below the LED 50 and co-operates with an adjacent phototransistor 60 to form a reflection light barrier. The operating wavelength of the LED 58 preferably is different from the operating wavelength of the LEDs 48 and 50.

The axis of the three light barriers are perpendicular to the plane of FIG. 1 and each intersects the axis of the test cell standing in front of the measuring head 28, i.e. is in an operating or measuring position.

Figure 3:
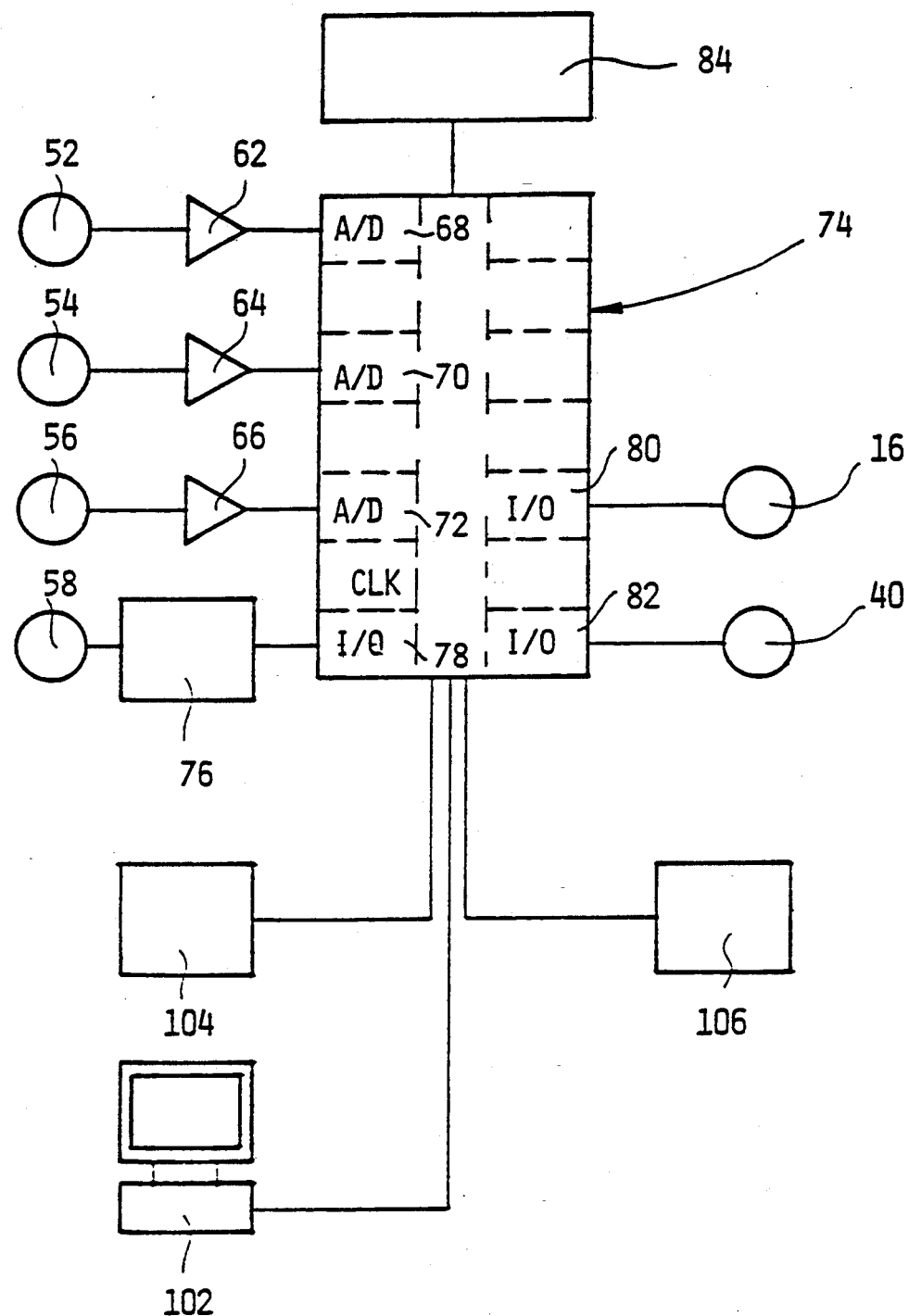
FIG. 3: is a block diagram of the evaluating electronics of the measuring apparatus.

As may be seen from FIG. 3, the phototransistors 52, 54, 60 are connected to narrow band a.c. amplifiers 62 to 62 tuned to the frequency of their supply voltages. These amplifiers also include a final rectifying stage and their output terminals are connected to input terminals of associated analog/digital converters 68, 70, 72 shown as printed circuit boards of an evaluating processor 74.

The rotary position sensor 42 is connected to an input/output board 78 of the evaluating processor 74 via an up/down counter 76. By means of further input/output boards 80, 82 the evaluating processor 74 controls the electric motor 16 and the electric motor 40.

The evaluating processor 74 co-operates with mass storage means 84, e.g. a hard disc drive. The mass storage means 84 is used to store the output signals regularly provided by the A/D-converters 68 through 72. Thus the mass storage means 84 stores the entire change in time of the blood corpuscle sedimentation processes of the various test cells 22 carried by the turn table 18. For each of the test cells 22 the entire profile of the optical density across the entire vertical extension of the test cell is stored for the three operating wavelengths and the different measuring times. From these values the respective position of the interphase defined between the serum and the blood cake can be deduced, e.g. by differentiation, and the position value can be additionally stored.

The mass storage means 84 further stores a plurality of different reference curves representing profiles of the optical density as they have been obtained for various reference samples, e.g. blood samples of healthy patients and of patients showing clear symptoms of given deseases. Furthermore among the reference curves there may be reference curves corresponding to typical sedimentation processes which can be treated theoretically. For example there are particular types of sedimentation processes and particularly types cf blood sedimentation, which can be represented by a growth curve or a Volterra curve.

Figure 5:
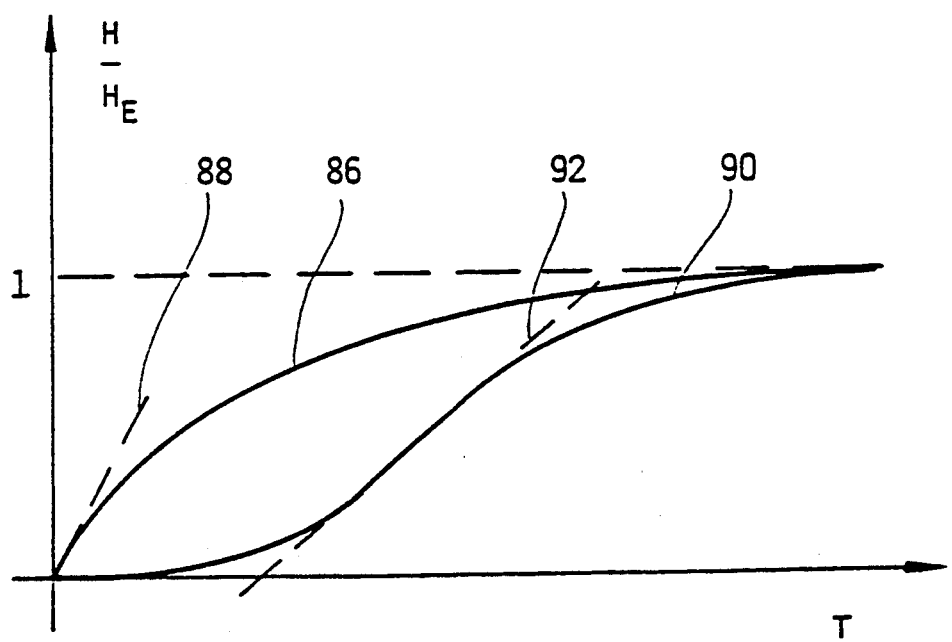
FIG. 5: is a schematic representation of two different types of sedimentation curves.

In FIG. 5 a growth curve is schematically shown at 86. It is characterized by its asymptotic value $h_E$ and the slope of its tangent 88 in the origin. At 90 a Volterra curve is shown, which can be characterized by its asymptotic value $h_e$ as well as the slope of its inflectional tangent 92 and e.g. the intersection of the latter with the time axis and with the asymptote $h=h_E$.

Figure 4:
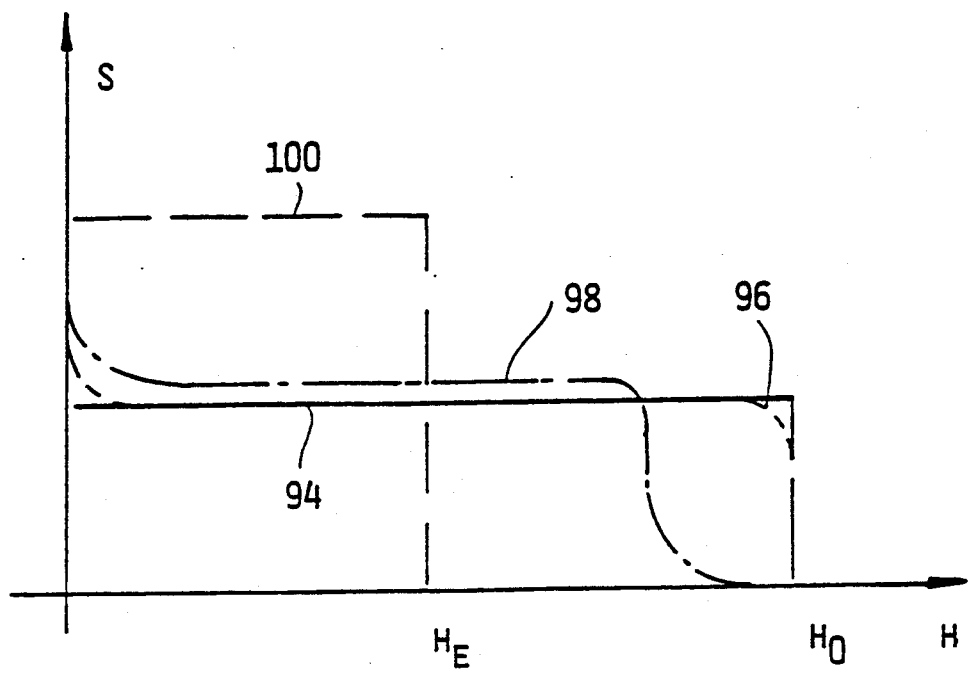
FIG. 4: is a schematic representation of the profile of the optical density in the beginning, shortly after the beginning and at the end of the sedimentation process.

FIG. 4 diagrammatically shows the development in time of the profile of the optical density along the test cell. In the beginning of the measuring process the optical density along the test cell is a constant as shown in full lines by curve 94. In a very first phase of the sedimentation process the blood corpuscles can freely move between other blood corpuscles in downward direction. The optical density in the uppermost portion of the test cell thus decreases. In the lowermost portion of the test cell the density shows a corresponding increase, since the blood corpuscles pile up in front of the bottom wall of the test cell. Both these density changes are shown in dashed lines by curve 96.

With increasing compacting of the blood corpuscles the respetively lower blood corpuscles represent an obstacle to the downward movement of the respectively upper corpuscles so that the already mentioned interphase between serum and blood cake is formed as shown in dot-and-dashed pattern by curve 98. Now the blood cake, which can be optically discerned from the upper serum will collapse until after a long measuring time the densest final arrangement of the blood corpuscles will be obtained, which is shown by the dashed curve 100.

The above description of the development in time of a sedimentation process, which has been made referring to FIG. 4, is only a rough qualitative picture and shows that blood sedimentation is a very complex non linear process. Particularly that portion of the sedimentation process, wherein the individual blood corpuscles can still best show their respective properties, is neglected in the classical way of determining the sedimentation rate (visual observation of the position of the interphase, only).

The evaluating processor 74 is connected to a monitor 102 continuously showing the intermediate results, which have been obtained so far, respectively. The monitor 102 also allows to eventually modify the program controlling the measuring program.

For documenting the values obtained at the end of the measuring process the evaluating processor 74 is connected to a printer 104 as well as to a plotter 106.

We claim:

1. An apparatus for measuring erythrocyte sedimentation rate, comprising test cell support means (18, 20, 24, 26) adapted to position at least one test cell (22) in parallel orientation with respect to the vertical direction, comprising a measuring head (36) measuring the optical density of blood and including at least one light barrier (48, 52), comprising head drive means (34, 40) for providing relative movement between the test cell support means and the measuring head in a direction parallel to the positioning direction of the test cells (22), a position sensor (42, 76) providing a position signal corresponding to the relative position of said at least one test cell (22) and measuring head (36), and an evaluating processor (74) which receives the output signals of the measuring head (36) as well as the position signal and continuously stores (84) the output signals of the measuring head (36) and the associated position signals and compares the stored position signals with at least one reference curve (6, 90; 94-100) and from this comparison extrapolates a presumable final value of the position of the interphase defined between the serum and the blood cake and also determines the sedimentation rate.

2. The measuring apparatus in accordance with claim 1, wherein the evaluating processor (74) compares the stored position signals with a plurality of different reference curves (86, 90; 94-100) and determines the final value of the interphase and sedimentation rate on the basis of the reference curve giving the best fit.

3. The measuring apparatus in accordance with claim 1 wherein the evaluating processor (74) furthermore calculates further characteristic data from the stored signals, including the starting point, the end point and the slope of linear portions of the sedimentation curve representing the change in time of the position of the interphase.

4. The measuring apparatus in accordance with claim 1, wherein the measuring head (36) comprises at least one further light barrier (50, 54), having an operating wavelength that is absorbed by the blood sample more strongly or more weakly than the operating wave length of the first light barrier (48, 50) and the evaluating processor (74) processes the measuring signals obtained from the further light barrier (50, 54) in the same way as the signals obtained from the first light barrier (48, 52).

5. The measuring apparatus as in claim 1, wherein each reference curve comprises a set of reference profiles of the optical density (94-100) covering the vertical extension of the test call.

6. The measuring apparatus as in claim 1, wherein among the light barriers there is at least one (48, 52; 50, 54) which is a transmission light barrier, the axis of which intersects the axis of the test cell.

7. The measuring apparatus as in claim 1, wherein the measuring head (36) comprises at least one reflection type light barrier (58, 60) and the evaluating processor (74) evaluates the measuring signals obtained therefrom in view of recognizing a bar code carried by the test cell (22).

8. The measuring apparatus in accordance with claim 7, wherein the test cell support means (18, 24, 26) comprises a plurality of receptacles (22) adapted to receive a test cell (22), and support drive means (14, 16) provided to intermittently move the test cell support means by a distance corresponding to the distance between two successive receptacles.

* * * * *